(12) United States Patent
Lauret

(10) Patent No.: US 10,048,119 B2
(45) Date of Patent: Aug. 14, 2018

(54) OPTICAL SYSTEM INTENDED TO MEASURE BRDF, BSDF AND BTDF

(71) Applicant: Jean-Pierre Lauret, Oyonnax (FR)

(72) Inventor: Jean-Pierre Lauret, Oyonnax (FR)

( * ) Notice: Subject to any disclaimer, the term of this patent is extended or adjusted under 35 U.S.C. 154(b) by 297 days.

(21) Appl. No.: 14/375,798

(22) PCT Filed: Jan. 21, 2013

(86) PCT No.: PCT/FR2013/050126
§ 371 (c)(1),
(2) Date: Jul. 31, 2014

(87) PCT Pub. No.: WO2013/114022
PCT Pub. Date: Aug. 8, 2013

(65) Prior Publication Data
US 2014/0375797 A1    Dec. 25, 2014

(30) Foreign Application Priority Data

Jan. 31, 2012 (FR) ..................................... 12 50886

(51) Int. Cl.
*G01N 21/47* (2006.01)
*G01J 1/04* (2006.01)
(Continued)

(52) U.S. Cl.
CPC ............ *G01J 1/0411* (2013.01); *G01N 21/47* (2013.01); *G01N 21/55* (2013.01); *G01N 21/59* (2013.01);
(Continued)

(58) Field of Classification Search
CPC ................................ G01N 21/59; G01N 21/55
See application file for complete search history.

(56) References Cited

U.S. PATENT DOCUMENTS

| 4,806,774 A | 2/1989 | Lin et al. |
| 6,804,001 B1 | 10/2004 | Eldin |

(Continued)

FOREIGN PATENT DOCUMENTS

| EP | 0294643 | 12/1988 |
| FR | 2749388 | 12/1997 |

(Continued)

OTHER PUBLICATIONS

Braat et al. "Aplanatic optical system containing two aspheric surfaces" Applied Optics vol. 18, No. 13 p. 2187.
Frolov et al "Design of aplanatic singlet for pickup" 2005 Optical Society of America.

*Primary Examiner* — Mehrdad Dastouri
*Assistant Examiner* — Rowina Cattungal
(74) *Attorney, Agent, or Firm* — Mark M. Friedman

(57) ABSTRACT

The optical system (1) is intended to measure the bidirectional reflectance and/or transmittance distribution function BRDF, BTDF and BSDF of a surface (10) of at least a portion of an object (7), the system comprising successively:
 an aplanatic lens (2) having an opening angle, the absolute value of which is comprised between 45° and a value strictly lower than 90°,
 a converging field lens (3) downstream of the plane P,
 an image pickup lens (4), the field angle of which is higher than or equal to the convergence angle of the scattered light beams emerging from the field lens, and
 a video sensor (5),
the aplanatic lens (2), the converging field lens (3), the image pickup lens (4) and the video sensor (5) being arranged so as to allow a conjugation C1 between the surface (10) and the entrance pupil of the image pickup lens (4) and a conjugation C2 between an intensity pattern and the video sensor (5).

14 Claims, 1 Drawing Sheet

(51) Int. Cl.
*G01N 21/55* (2014.01)
*G02B 27/14* (2006.01)
*G01N 21/59* (2006.01)

(52) U.S. Cl.
CPC ..... *G02B 27/144* (2013.01); *G01N 2021/559* (2013.01)

(56) References Cited

U.S. PATENT DOCUMENTS

| | | | | |
|---|---|---|---|---|
| 2004/0105619 | A1* | 6/2004 | Weaver | G02B 6/29394 385/37 |
| 2006/0023202 | A1* | 2/2006 | Delacour | G01N 21/55 356/121 |
| 2009/0296204 | A1* | 12/2009 | Schuster | G02B 17/0812 359/708 |
| 2010/0157441 | A1* | 6/2010 | Kweon | G02B 3/02 359/708 |
| 2013/0296649 | A1* | 11/2013 | Kirma | A61B 1/00177 600/109 |

FOREIGN PATENT DOCUMENTS

| | | |
|---|---|---|
| FR | 2749388 A1 | 12/1997 |
| FR | 2860869 | 4/2005 |
| JP | H11505928 A | 5/1999 |
| JP | H11211660 A | 8/1999 |

* cited by examiner

OPTICAL SYSTEM INTENDED TO MEASURE BRDF, BSDF AND BTDF

The present invention relates to an optical system, intended to measure the bidirectional reflectance and/or transmittance distribution functions BRDF, BTDF and BSDF of a surface which is reflective and/or operating in transmission, of at least a portion of an object. Furthermore, the present invention also relates to a device for measuring the luminous intensity of a surface which is reflective and/or operating in transmission, of at least a portion of an object.

Traditionally, the functions of bidirectional reflectance distribution, BRDF (English acronym of 'bidirectional reflectance distribution function') or of bidirectional transmittance distribution, BTDF (English acronym of 'bidirectional transmittance distribution function') or the function of bidirectional scattering, BSDF (English acronym of 'bidirectional scattering distribution function', the BSDF combining the BRDF and the BTDF into one single function), are measured with a two-axis goniometer. The intensity of the scattered light is measured point by point with a large-sized articulated arm movable in all directions of space. Consequently, several hours are necessary to perform a complete measurement. In addition, the two-axis goniometer is bulky, heavy and difficult to transport. It is used only in the laboratory and is not suitable for the on-site measurement.

Hence, it seems appropriate to propose a double-conjugate system for measuring BRDF, BTDF and BSDF, which is compact, without moving portion, less expensive, and the measurement of which is quick.

Document FR2860869 (J. Delacour—OPTIS) describes a device for measuring the luminous intensity of an object which comprises a dioptric central portion for example constituted by an converging aspherical lens and a catadioptric peripheral portion such as a parabolic reflector perforated on its top. The converging aspherical lens and the parabolic reflector are arranged so that their optical axes H and their focuses F1 coincide. The object, the luminous intensity or the BRDF, BTDF or BSDF of which is to be measured, is placed at this focus F1. Light scattered by the object is collected either by the converging aspherical lens (when the light rays are slightly inclined relative to the optical axis H), or by the parabolic reflector (when the light rays are strongly inclined relative to the optical axis H). The boundary between slightly inclined and strongly inclined is located in the vicinity of 30 degrees of angle. Thus, document FR2860869 describes a measuring device less bulky than the goniometer but this device does not allow obtaining a good resolution in particular at large scattering angles because it is designed around a point object and it does not take into account all opening aberrations (coma) and field aberrations (field curvature). One consequence is that the resolution is not constant according to the angle of the performed measurement. In addition, the discontinuity between the lens and the parabolic reflector creates an artifact which disturbs the measurement.

Document FR2749388 (T. Leroux—ELDIM) describes an BRDF measuring apparatus which is limited to a low field angle. Indeed, the measuring lens performs the Fourier transform which implicitly induces a good correction of the opening aberrations and field aberrations but the fact that the diameter of the light beam has always the same section, regardless of the considered angle, limits the opening angle to 40°. This implies that the sum of the angles of the incident light and of the scattered light does not exceed the opening angle of the measuring lens, namely 40°. Consequently, surfaces the scattering angle of which exceeds 40°, in particular highly diffuse surfaces, cannot be measured with this device.

One of the aims of the invention is to overcome one or several of these drawbacks. To this end, and according to a first aspect, the invention has for object an optical system, intended to measure the bidirectional diffuse functions BRDF, BTDF and BSDF of a surface which is reflective and/or operating in transmission, of at least a portion of an object, the system comprising successively in the direction of propagation of the scattered light:

an aplanatic lens having an opening angle the absolute value of which is comprised between 45° and a value strictly lower than 90°, capable of projecting the image of an intensity pattern of the light scattered by the surface which is reflective and/or operating in transmission, on an intermediate observation plane P downstream of the aplanatic lens, a converging field lens downstream of the plane P, an image pickup lens, the field angle of which is higher than or equal to the convergence angle of the scattered light beams emerging from the field lens, and a video sensor, the aplanatic lens, the converging field lens, the image pickup lens and the video sensor being arranged so as to allow a first conjugation between the surface which is reflective and/or operating in transmission, and the entrance pupil of the image pickup lens and a second conjugation between an intensity pattern of the scattered light and the video sensor.

Thus, this configuration allows obtaining a sharp image of an intensity pattern of the scattered light thanks to the two conjugations obtained by the system, when the focusing of the image pickup lens is performed.

By "aplanatic lens" we mean a lens having an angular resolution comprised between 10° and a value strictly higher than 0° and preferably comprised between 5° and a value strictly higher than 0° and still preferably comprised between 1° and a value strictly higher than 0° so that the correction of the opening aberrations is adapted to the angular resolution of the measurement.

When the lens is rigorously aplanatic (or the angular resolution of which is comprised between 1° and a value strictly higher than 0°), the opening aberrations of the first conjugation are corrected. Thus the spherical aberration is corrected at all levels and the optical path between the object focus and the intermediate observation plane P is always identical. This condition (also called rigorous stigmatism) translates into the following formula: $\Sigma n_i * e_i$=constant, where $e_i$ represents the thickness of the material through which light travels along a light ray, and $n_i$ the associated refractive index. Moreover, the coma aberration is corrected at all levels, such that the height h between the emergent ray and the optical axis H may be defined by the equation "h=f sin α" with f designating the focal length of the lens and α designating the opening angle of the considered ray.

In this way, the system according to the invention allows measuring the BRDF, BTDF and BSDF of a wide variety of diffusing surfaces, from low diffusing surfaces to high diffusing surfaces according to the considered opening angle. Furthermore, the resolution of the measurements is very good for small or large sizes of studied surface such as 2 mm of diameter while proposing a system which is compact, without moving portions and with a very short measuring time.

According to one embodiment of the invention, the converging field lens is aplanatic so that the first conjugation as a whole is aplanatic, so as to improve the resolution of the optical system and to properly delimit the actually measured surface of the diffusing object.

According to another embodiment, the converging field lens comprises at least two lenses arranged so that the converging field lens is aplanatic so as to simplify the optical design.

According to one possibility, the field lens has a thickness and a camber the value of which is higher than 10% of the focal length of the converging field lens so as to be able to create a negative field curvature and compensate the field curvature of the aplanatic lens. Indeed, the negative curvature of the field lens allows compensating the positive field curvature of the aplanatic lens so as to correct the second conjugation of the field curvature and improve the angular resolution for high scattering angles.

Alternatively, the converging field lens is a single spherical or aspherical lens, of the biconvex or plano-convex type, so as to gain size and easiness of realization but in that case, the second conjugation is not corrected for field aberrations, in particular the field curvature because its field curvature is not controlled.

The aplanatic lens has for example an opening angle, the absolute value of which is comprised between 0 and a value strictly lower than 90°, preferably the absolute value of which is comprised between 45° and a value strictly lower than 90°, and more preferably the absolute value of which is comprised between 60° and a value strictly lower than 90°, and still more preferably the absolute value of which is comprised between 85° and a value strictly lower than 90° so as to be able to observe a wide variety of scattering surfaces and in particular highly diffusing surfaces.

According to an embodiment, the aplanatic lens comprises at least one aspherical lens, preferably, the aplanatic lens comprises two aspherical lenses, and still preferably the aplanatic lens comprises two aspherical lenses, each of the surfaces of which has a deviation relative to the local curvature radius measured at the center of its surface, which is higher than or equal to 10% of the focal distance of the aplanatic lens.

Therefore, when the aplanatic lens is thus constituted of two highly aspherical lenses, its opening angle is very significant. Thus, when the first and second conjugations are corrected for opening and field aberrations, it is possible to observe an extended surface (2 mm for example) and to have a good angular resolution as well as a reduced size. In addition, the image of a Lambertian intensity pattern gives a uniform light distribution on the video sensor, which maximizes the dynamics. Furthermore, all the scattered light is recovered by the video sensor and there is no vignetting which allows limiting the sensitivity problems during the measurement of the surface which is reflective and/or operating in transmission, of dark objects. Moreover, the apparent surface of the object seen by the sensor is always the same during a same measurement, regardless of the observation angle, so that the surface is always identical during the measurement. Finally, the measurement at high angles of incidence is done with a good resolution.

In the event that the aplanatic lens is constituted of one single aspherical lens, the cost and the size are reduced, but the opening angle is limited to +/−45° which limits measuring to low diffusing surfaces.

According to one alternative embodiment, the aplanatic lens comprises at least two lenses arranged so as to correct opening aberrations of the aplanatic lens. Said at least two lenses may be of any kind, spherical or aspherical, converging or diverging.

Advantageously, the aplanatic lens has a conjugation of the infinite focus type so that it is possible to create the image of an intensity pattern located at infinity on an intermediate observation plane P and to match a direction of the intensity pattern with a pixel of the video sensor.

According to another embodiment, the image pickup lens has a field angle of +/−20°.

In particular the image pickup lens is a camera lens.

The video sensor is for example chosen among a sensor of the CMOS type or of the CCD type.

By the expression 'CCD' which is the English acronym of 'Charge-Coupled Device', we mean a charge transfer device.

By the expression 'CMOS' type video sensor', we mean a sensor with CMOS components which is the English acronym of 'Complementary Metal Oxide Semiconductor'.

According to another aspect, the invention also relates to a device for measuring bidirectional diffuse functions BRDF, BTDF and BSDF of a surface which is reflective and/or operating in transmission, of at least a portion of an object comprising:
  an optical system as previously described, and
  an illumination path capable of illuminating the surface which is reflective and/or operating in transmission, at several angles of incidence i, so as to be able to measure the intensity pattern of the light scattered by the surface which is reflective and/or operating in transmission, on the video sensor.

By the expression 'illumination path', we mean the propagation of light beams from the set of light source toward at least a portion of the object.

Advantageously, the measuring device includes means for reconstituting the BRDF, BTDF and BSDF of the surface which is reflective and/or operating in transmission, and means for recording measurements of the BRDF, BTDF and BSDF on a medium.

The reconstitution means may be a software for example. The recording means allow constituting a data library of the measured BRDF, BTDF and BSDF which could be used in creating synthetic image to obtain a faithful reproduction of the object.

According to a particular embodiment, the measuring device is adapted to measure bidirectional diffuse functions BRDF and the illumination path comprises:
  a set of light sources of pre-collimated beams,
  a set of converging lenses arranged so as to form the image of the light sources on the intermediate observation plane P, and
  a semi-reflective plate disposed at the intermediate observation plane P so that the pre-collimated beams are reflected toward at least a portion of the object through the aplanatic lens while allowing the passage of the scattered light from the object or a portion of the object toward the video sensor. Indeed, by focusing the beams of the light sources on the intermediate observation plane P, it is possible to address several given angles of incidence.

Other aspects, aims and advantages of the present invention will become more apparent upon reading the following description of an embodiment thereof, given by way of non-limiting example and made with reference to the accompanying drawings. The figures do not necessarily comply with the scale of all the represented elements so as to improve their readability. In the following description, for simplicity, identical, similar or equivalent elements of the different embodiments have the same reference numerals.

Figure 1:
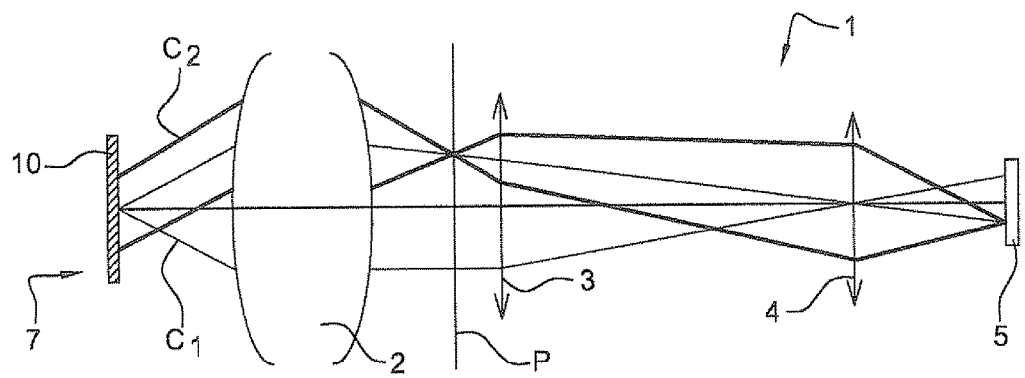
FIG. 1 illustrates a schematic diagram of the optical system according to one embodiment of the invention.

FIG. 1 illustrates an optical system 1 comprising successively an aplanatic lens 2, a converging field lens 3, an image pickup lens 4 and a video sensor 5.

The substantially aplanatic lens 2, i.e. the angular resolution of which is comprised between 1° and a value strictly higher than 0 or namely a lens 2 corrected for opening aberrations (spherical and coma aberrations), has a conjugation of the infinite focus type. It is furthermore provided with a very significant opening angle that may range from 0 to a value close to +/−90° so as to measure low or highly diffusing surfaces. To do this, the aplanatic lens 2 is constituted of two aspherical lenses 6. It may also be constituted of one single aspherical lens 6 so as to reduce costs but the opening angle of such a lens 2 is limited to +/−45°.

When the aplanatic lens 2 comprises at least two aspherical lenses 6, their surfaces are difficult to determine, in particular for large opening angles. The parameterization requires resolving a problem with two equations (the spherical aberration and the coma) and four unknowns (the four optical surfaces). Theoretically, we can hence define only two of the four optical surfaces. Practically, the two free surfaces are adjusted so as to obtain a physically achievable geometry. The optimization calculation of a predefined geometry (of the polynomial or conic type) using an optical calculation software does not give satisfactory results for obtaining a lens provided with a good resolution at the significant opening angles. However, the analytical calculation allows defining a differential equation which may be numerically resolved by a software and leads to the complete definition of two of the four surfaces of the lenses 6 for a perfectly aplanatic lens 2, knowing that the two other surfaces are used as parameters. This differential equation is obtained by analytical calculation based on the two following formulas:

$\Sigma n_i * e_i$ =constant, where $e_i$ represents the thickness of the material through which light travels along a light ray, from the object focus to the intermediate observation plane P (correction of the spherical aberration), and $n_i$ the associated refractive index.

h=f sin α with f designating the focal length of the lens, a designating the opening angle of an incident ray and h the height between the corresponding emergent ray and the optical axis H (correction of the coma).

Let (x1, y1, x2, y2) be the coordinates of the two surfaces that are not considered as parameters. By propagating a light beam through the lens from the focus to the intermediate observation plane P, it is possible to reformulate the two preceding equations by introducing the unknowns (x1, y1, x2, y2). The result is a set of coupled equations dependent of (x1, y1, x2, y2). One of these equations is a differential equation which is numerically resolved, using an opening angle ray of 0° as an initial condition.

The case of an aplanatic lens constituted of one single aspherical lens 6 is dealt with in the same manner, but this time there are two equations, two unknowns and no free parameter. According to a first conjugation C1 performed by the optical system 1 (the thinnest tracing of rays), the light scattered by the surface 10 which is reflective and/or operating in transmission, of a portion of the object 7 propagates through the aplanatic lens 2. This has the effect that an intensity pattern of the scattered light is projected on an intermediate observation plane P located upstream of the converging field lens 3. This field lens 3 then converges the light beams of this image in the image pickup lens 4. The converging field lens 3 is an aplanatic lens so that the conjugation C1 in its whole is aplanatic. Alternatively, the lens 3 may be constituted of one single lens of the aspherical condenser type for limiting costs.

According to a second conjugation C2 performed by the optical system 1 (the widest tracing of rays), a direction of the intensity pattern located at infinity matches a pixel of the video sensor 5. This second conjugation C2 is corrected for aberrations of field curvature induced by the aplanatic lens 2 thanks to a field lens 3, the thickness and camber of which are significant. They are in fact higher than 10% of the focal length of the lens. The thickness and the camber of the field lens 3 are determined so as to introduce a negative field curvature which compensates the positive field curvature of the aplanatic lens 2.

Figure 2:
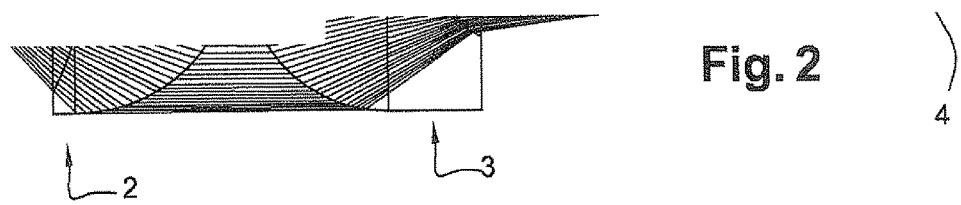
FIG. 2 illustrates a tracing of rays through an aplanatic lens and a field lens, from a source point located at the center of the object, to the image pickup lens (conjugation C1) according to one embodiment of the invention.

Referring to FIG. 2, a tracing of rays through the aplanatic lens 2 and the field lens 3 illustrates the first conjugation C1. The source point is located at the object focus of the aplanatic lens 2. This figure illustrates in particular the intermediate observation plane P which is actually a curve due to the field aberrations of the aplanatic lens 2, which are approximately corrected by the negative field curvature of the thick converging field lens 3.

Figure 3:
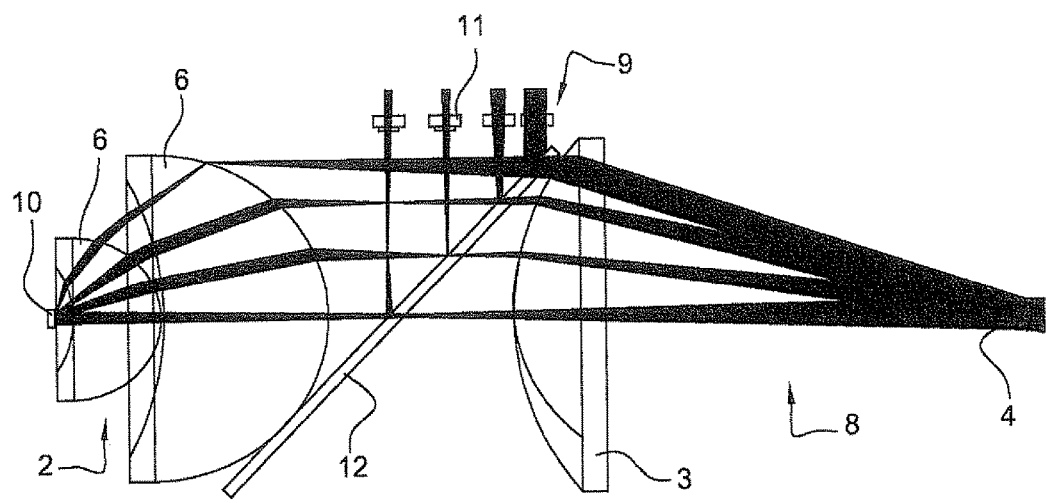
FIG. 3 illustrates a tracing of rays from the intensity pattern toward the video sensor (conjugation C2), with the superimposed illumination paths according to one embodiment of the invention.

Referring to FIG. 3 is illustrated a device 8 for measuring the BRDF. In addition to the optical system 1 as precedingly described, the measuring device 8 comprises an illumination path 9 constituted of a set of four light sources of pre-collimated beams, such as 3 min encapsulated LEDs, but a different number of light sources is possible. FIG. 3 illustrates four converging lenses 11 corresponding to the light sources so as to focus the pre-collimated beams on the intermediate observation plane P thanks to a semi-reflective plate 12 interposed between the aplanatic lens 2 and the field lens 3.

These converging lenses 11 are defined while taking into account the curvature of the intermediate observation plane P so as to not degrade the angular resolution of the illumination path 9. Light thus propagates toward the reflective surface 10 of the portion of the object 7 to be measured. Then, light scattered by the reflective surface 10 of the object 7 propagates from the object to the video sensor 5.

According to a not illustrated embodiment, when the measuring device 8 is applied to measuring the BTDF function, the light sources emit collimated beams upstream of the surface 10 operating in transmission. Thus, the surface 10 is illuminated with predetermined angles of incidence i, each light source having a divergence of at least 1° so as to match the angular resolution of the measuring device (8). The angles of incidence obtained by the aplanatic system when the measuring device 8 is used for measuring the BRDF are this way also obtained for measuring the BTDF.

It goes without saying that the invention is not limited to the embodiment described above by way of example but that it comprises all technical equivalents and alternatives of the means described as well as their combinations.

The invention claimed is:

1. An optical system comprising successively in the direction of propagation of the light scattered by a surface:

an entrance pupil located at the surface, which is reflective and/or operating in transmission, of at least a portion of an object;
   an aplanatic lens forming a sharp image of the object, the aplanatic lens having an opening angle, the absolute value of which is between 45° and a value strictly lower than 90°, and having an angular resolution between 10° and a value strictly higher than 0°, such that, correction of aberrations of the opening of the aplanatic lens is adapted to the angular resolution of a measurement of the optical system, the aplanatic lens projecting the image of an intensity pattern of the light scattered by the surface on an intermediate observation plane P downstream of the aplanatic lens;
   a converging field lens downstream of the plane P, the converging lens having a thickness and a camber, their respective values being higher than 10% of the focal length of the converging field lens so as to be able to create a negative field curvature and compensate the field curvature of the aplanatic lens;
   an image pickup lens, the field angle of which is higher than or equal to the convergence angle of the scattered light beams emerging from the converging field lens; and
   a video sensor having multiple pixels,
   the aplanatic lens, the converging field lens, the image pickup lens and the video sensor being arranged so as to allow a first conjugation between the surface of the object and the entrance pupil of the image pickup lens, and a second conjugation between the an intensity pattern of the scattered light and the video sensor whereby portions of the intensity pattern emanating from the same direction from the surface of the object are matched to the same pixel of the video sensor, and wherein the first conjugation is aplanatic, and wherein the optical system is constructed for measuring the bidirectional reflectance distribution function (BRDF), the bidirectional transmittance distribution function (BTDF) and/or the bidirectional scattering distribution function (BSDF) of the surface.

2. The optical system according to claim 1, wherein the converging field lens is aplanatic.

3. The optical system according to claim 2, wherein the converging field lens comprises at least two lenses arranged so that the converging field lens is aplanatic.

4. The optical system according to claim 1, wherein the converging field lens comprises at least two lenses arranged so that the converging field lens is aplanatic.

5. The optical system according to claim 1, wherein the absolute value of the opening angle of the aplanatic lens is between 60° and a value strictly lower than 90° or is between 85° and a value strictly lower than 90°.

6. The optical system according to claim 1, wherein the aplanatic lens comprises two aspherical lenses, each of the surfaces of which has a deviation relative to the local curvature radius measured at the center of its surface, which is higher than or equal to 10% of the focal length of the aplanatic lens.

7. The optical system according to claim 1, wherein the aplanatic lens has a conjugation of the infinite focus type.

8. A device for measuring the bidirectional reflectance distribution function (BRDF), the bidirectional transmittance distribution function (BTDF) and/or the bidirectional scattering distribution function (BSDF) of a surface which is reflective and/or operating in transmission, of a at least a portion of an object comprising: an optical system according to claim 1; and an illumination path for illuminating the surface which is reflective and/or operating in transmission, at several angles of incidence.

9. The device according to claim 8, wherein the device includes means for reconstituting the BRDF, BTDF and BSDF of the surface which is reflective and/or operating in transmission, and means for recording, on a medium, measurements of the BRDF, BTDF and BSDF.

10. The device according to claim 9, wherein the illumination path comprises:
   a set of light sources of pre-collimated beams;
   a set of converging lenses arranged so as to focus the light sources on the intermediate observation plane P; and
   a semi-reflective plate disposed at the intermediate observation plane P so that the pre-collimated beams are reflected toward at least a portion of the object through the aplanatic lens while allowing the passage of the scattered light from the object or a portion of the object toward the video sensor.

11. The device according to claim 8, wherein the illumination path comprises:
   a set of light sources of pre-collimated beams;
   a set of converging lenses arranged so as to focus the light sources on the intermediate observation plane P; and
   a semi-reflective plate disposed at the intermediate observation plane P so that the pre-collimated beams are reflected toward at least a portion of the object through the aplanatic lens while allowing the passage of the scattered light from the object or a portion of the object toward the video sensor.

12. The optical system according to claim 1, wherein the light beams passing through the aplanatic lens and the converging field lens are non-collimated.

13. An optical system comprising successively in the direction of propagation of the light scattered by the surface: an entrance pupil located at the surface, which is reflective and/or operating in transmission, of at least a portion of an object; an aplanatic lens forming a sharp image of the object, the aplanatic lens having an opening angle, the absolute value of which is between 45° and a value strictly lower than 90°, and having an angular resolution between 10° and a value strictly higher than 0°, such that, correction of aberrations of the opening of the aplanatic lens is adapted to the angular resolution of a measurement of the optical system, the aplanatic lens projecting the image of an intensity pattern of the light scattered by the surface on an intermediate observation plane P downstream of the aplanatic lens, wherein the aplanatic lens has a conjugation of the infinite focus type; a converging field lens downstream of the plane P; an image pickup lens, the field angle of which is higher than or equal to the convergence angle of the scattered light beams emerging from the converging field lens; and a video sensor having multiple pixels, the aplanatic lens, the converging field lens, the image pickup lens and the video sensor being arranged so as to allow a first conjugation between the surface of the object and the entrance pupil of the image pickup lens, and a second conjugation between the intensity pattern of the scattered light and the video sensor whereby portions of the intensity pattern emanating from the same direction from the surface of the object are matched to the same pixel of the video sensor, and wherein the first conjugation is aplanatic, and wherein the optical system is constructed for measuring the bidirectional reflectance distribution function (BRDF), the bidirectional transmittance distribution function (BTDF) and/or the bidirectional scattering distribution function (BSDF) of the surface.

14. An optical system comprising successively in the direction of propagation of the light scattered by the surface:

an entrance pupil located at the surface, which is reflective and/or operating in transmission, of at least a portion of an object; an aplanatic lens forming a sharp image of the object, the aplanatic lens having an opening angle, the absolute value of which is between 45° and a value strictly lower than 90°, and having an angular resolution between 10° and a value strictly higher than 0°, such that, correction of aberrations of the opening of the aplanatic lens is adapted to the angular resolution of a measurement of the optical system, the aplanatic lens projecting the image of an intensity pattern of the light scattered by the surface on an intermediate observation plane P downstream of the aplanatic lens; a converging field lens downstream of the plane P, the converging lens being aplanatic; an image pickup lens, the field angle of which is higher than or equal to the convergence angle of the scattered light beams emerging from the converging field lens; and a video sensor having multiple pixels, the aplanatic lens, the converging field lens, the image pickup lens and the video sensor being arranged so as to allow a first conjugation between the surface of the object and the entrance pupil of the image pickup lens, and a second conjugation between the intensity pattern of the scattered light and the video sensor whereby portions of the intensity pattern emanating from the same direction from the surface of the object are matched to the same pixel of the video sensor, and wherein the first conjugation is aplanatic, and wherein the optical system is constructed for measuring the bidirectional reflectance distribution function (BRDF), the bidirectional transmittance distribution function (BTDF) and/or the bidirectional scattering distribution function (BSDF) of the surface.

\* \* \* \* \*